United States Patent
Williams

(10) Patent No.: US 9,031,667 B2
(45) Date of Patent: May 12, 2015

(54) MINIMAL DEVICE AND METHOD FOR EFFECTING HYPERTHERMIA DERIVED ANESTHESIA

(75) Inventor: Donald V. Williams, Woodford (AU)

(73) Assignee: InterventionTechnology Pty Ltd, Richmond, VIC (AU)

( * ) Notice: Subject to any disclaimer, the term of this patent is extended or adjusted under 35 U.S.C. 154(b) by 1948 days.

(21) Appl. No.: 11/912,147

(22) PCT Filed: Mar. 6, 2006

(86) PCT No.: PCT/AU2006/000276
§ 371 (c)(1),
(2), (4) Date: Oct. 20, 2007

(87) PCT Pub. No.: WO2006/092021
PCT Pub. Date: Sep. 8, 2006

(65) Prior Publication Data
US 2008/0262490 A1  Oct. 23, 2008

(30) Foreign Application Priority Data
Mar. 4, 2005 (AU) .............................. 2005901046

(51) Int. Cl.
| | |
|---|---|
| *A61F 2/00* | (2006.01) |
| *A61F 7/12* | (2006.01) |
| *A61B 18/04* | (2006.01) |
| *A61B 18/18* | (2006.01) |
| *A61B 18/14* | (2006.01) |
| *A61N 1/40* | (2006.01) |

(Continued)

(52) U.S. Cl.
CPC ... *A61B 18/1477* (2013.01); *A61B 2018/00434* (2013.01); *A61B 2018/00702* (2013.01); *A61B 2018/00875* (2013.01); *A61B 2018/143* (2013.01); *A61N 1/06* (2013.01); *A61N 1/36017* (2013.01); *A61N 1/36021* (2013.01); *A61N 1/403* (2013.01)

(58) Field of Classification Search
USPC ......... 607/96–102, 115–118, 113; 606/27–52
See application file for complete search history.

(56) References Cited

U.S. PATENT DOCUMENTS 4,188,927 A * 2/1980 Harris .............................. 606/38
4,682,596 A * 7/1987 Bales et al. ..................... 606/39

(Continued)

OTHER PUBLICATIONS

Franco, Sergio, Electric Circuit Fundamentals, Saunders College Publishing, 1994. pp. 526-527,581-583.

(Continued)

*Primary Examiner* — Ronald Hupczey
*Assistant Examiner* — Adam Avigan
(74) *Attorney, Agent, or Firm* — Moore Patents; David Dreyfuss; Cynthia R. Moore

(57) ABSTRACT

A method and device for inducing anaesthesia in mammals by the application of RF energy to create hyperthermia derived neural anaesthesia. An RF generator drives a plurality of electrodes placed in tissue surrounding the target nerve fiber to desiccate the desired length of nerve fiber to be desiccated in a single deployment. The device allows high-speed selection/de-selection of bipolar electrode pairs or sets under continuous RF excitation. Activation of electrode pairs is adapted in response to sensed current density and temperature (by electrodes not in the current discharge activation phase) in order to create lesions of complex and well defined shape necessary for the production of hyperthermia derived neural anaesthesia.

22 Claims, 6 Drawing Sheets

(51) Int. Cl.
*A61B 18/00* (2006.01)
*A61N 1/06* (2006.01)
*A61N 1/36* (2006.01)

(56) References Cited

U.S. PATENT DOCUMENTS

| | | | |
|---|---|---|---|
| 5,438,302 A * | 8/1995 | Goble | 331/167 |
| 5,647,869 A * | 7/1997 | Goble et al. | 606/37 |
| 5,769,847 A * | 6/1998 | Panescu et al. | 606/42 |
| 6,093,186 A * | 7/2000 | Goble | 606/34 |
| 6,241,701 B1 * | 6/2001 | Hofmann | 604/21 |
| 6,319,249 B1 * | 11/2001 | Tollner | 606/34 |
| 6,648,883 B2 * | 11/2003 | Francischelli et al. | 606/41 |
| 6,663,622 B1 * | 12/2003 | Foley et al. | 606/34 |
| 7,282,049 B2 * | 10/2007 | Orszulak et al. | 606/34 |
| 7,363,071 B2 * | 4/2008 | Damasco et al. | 600/427 |
| 2003/0109871 A1 * | 6/2003 | Johnson et al. | 606/42 |
| 2005/0283148 A1 * | 12/2005 | Janssen et al. | 606/34 |
| 2006/0015095 A1 * | 1/2006 | Desinger et al. | 606/41 |

OTHER PUBLICATIONS

"Q factor," Wikipedia article retrieved Aug. 12, 2012.

* cited by examiner

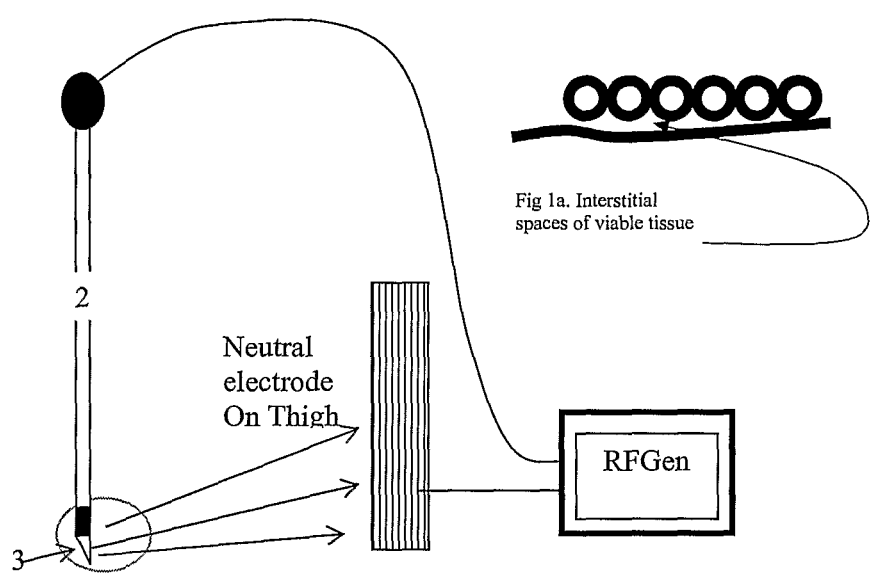
Fig. 1 – Contemporary mono-polar Device & practice
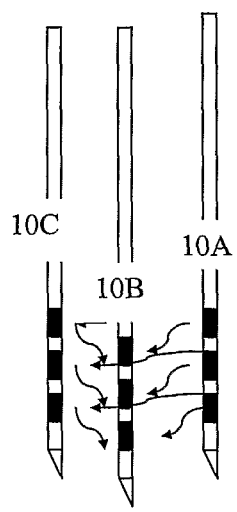
Fig 2. Contemporary Cardiac bipolar needle system in fixed spatial arrangement

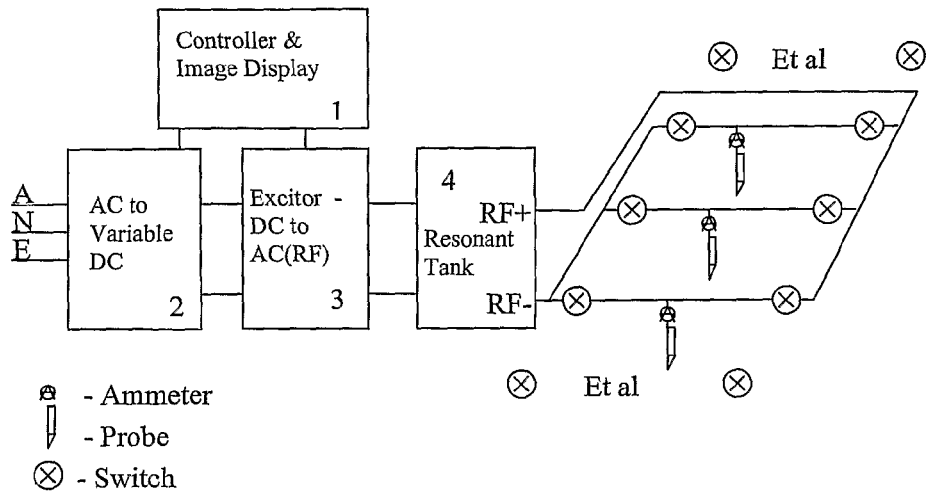
Fig 3 Showing basic functional blocks with only three electrodes each with current measurement facility.
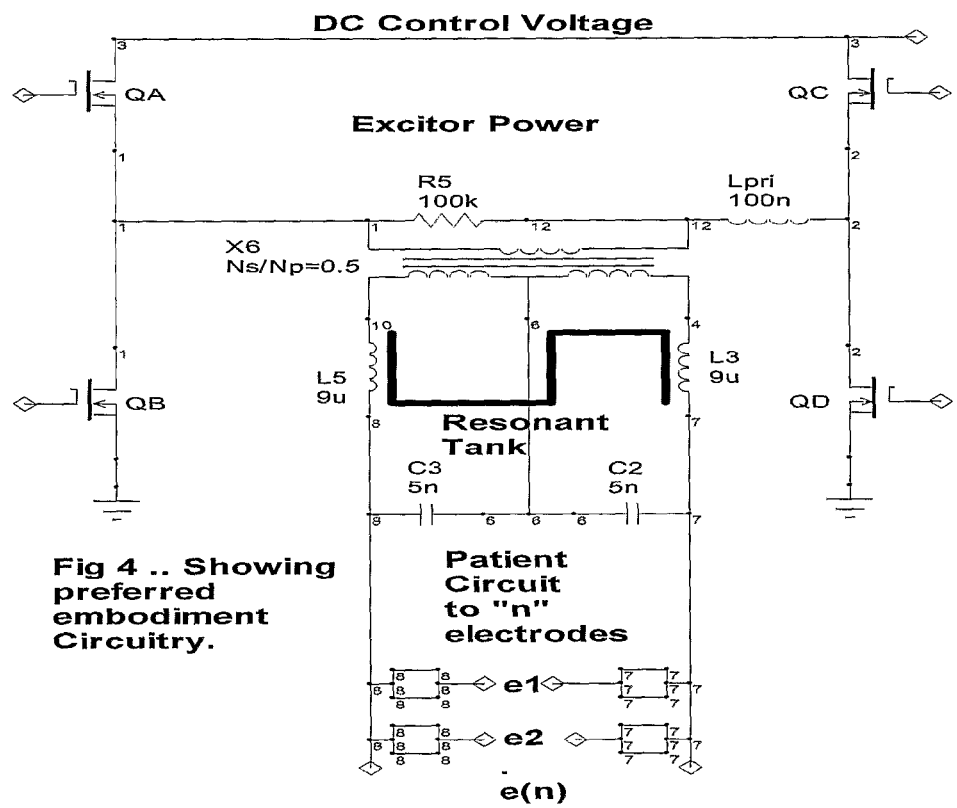
Fig 4 .. Showing preferred embodiment Circuitry.

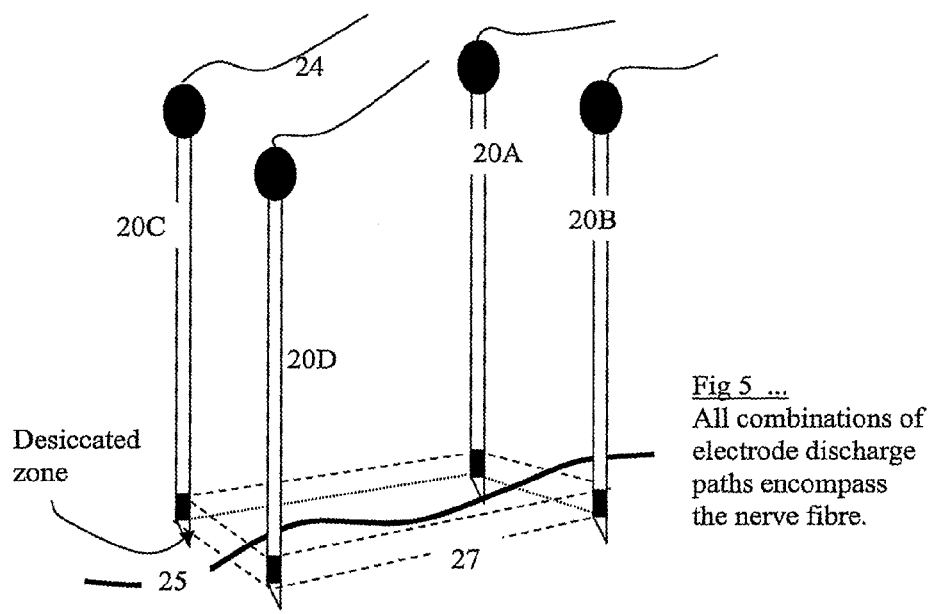
Fig 5 ...
All combinations of electrode discharge paths encompass the nerve fibre.
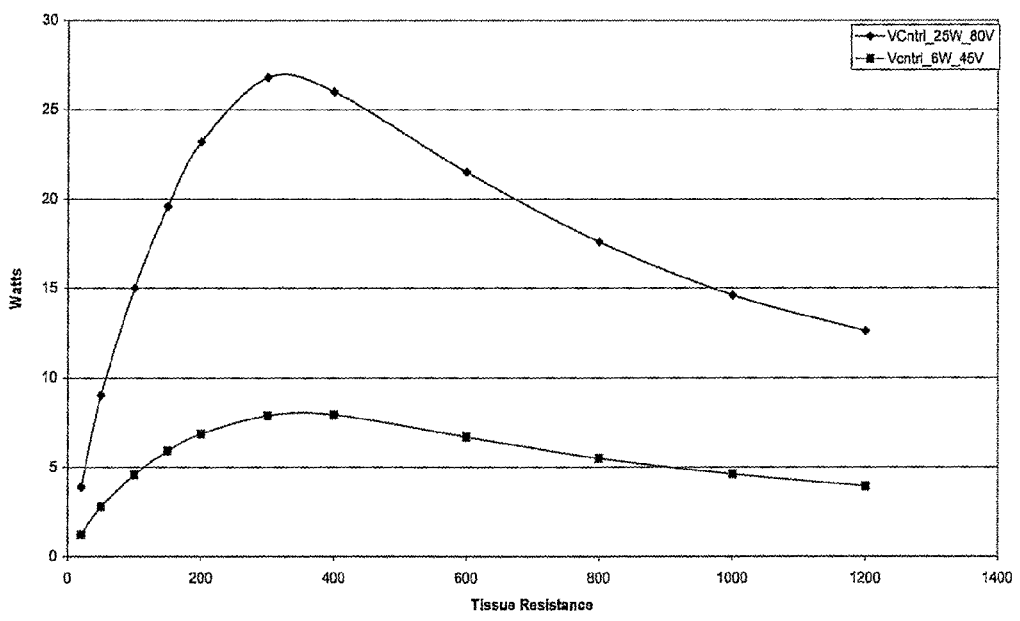

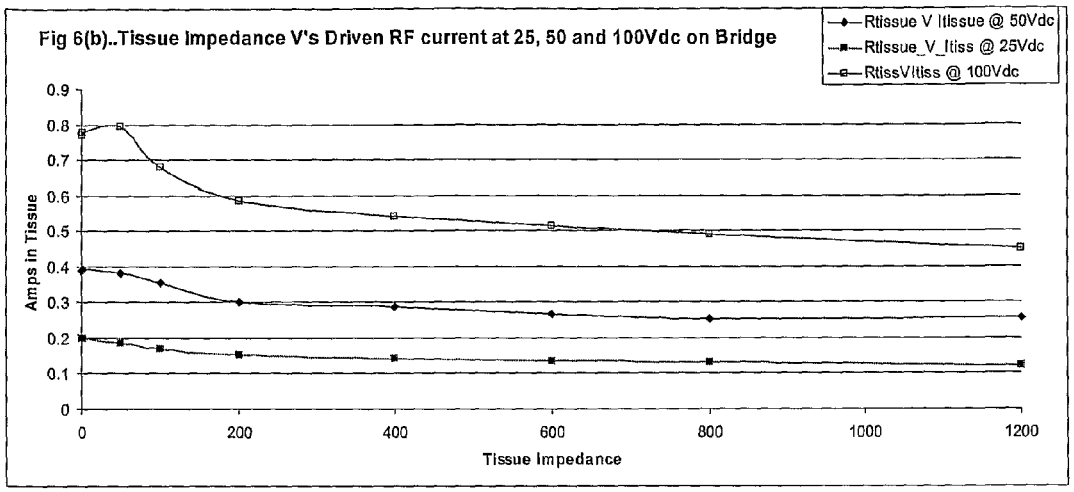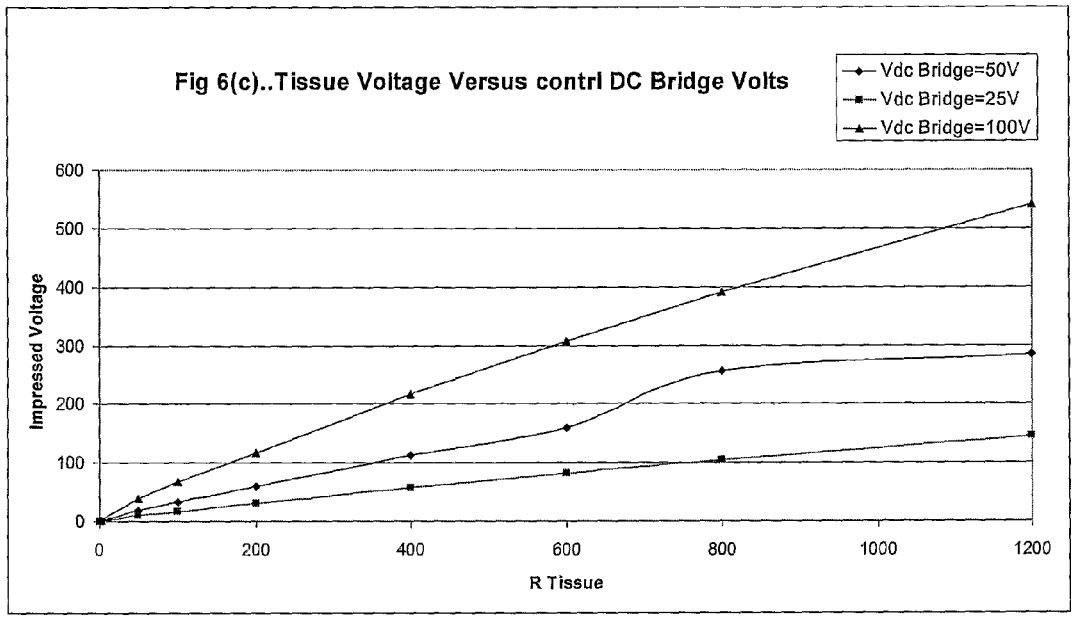

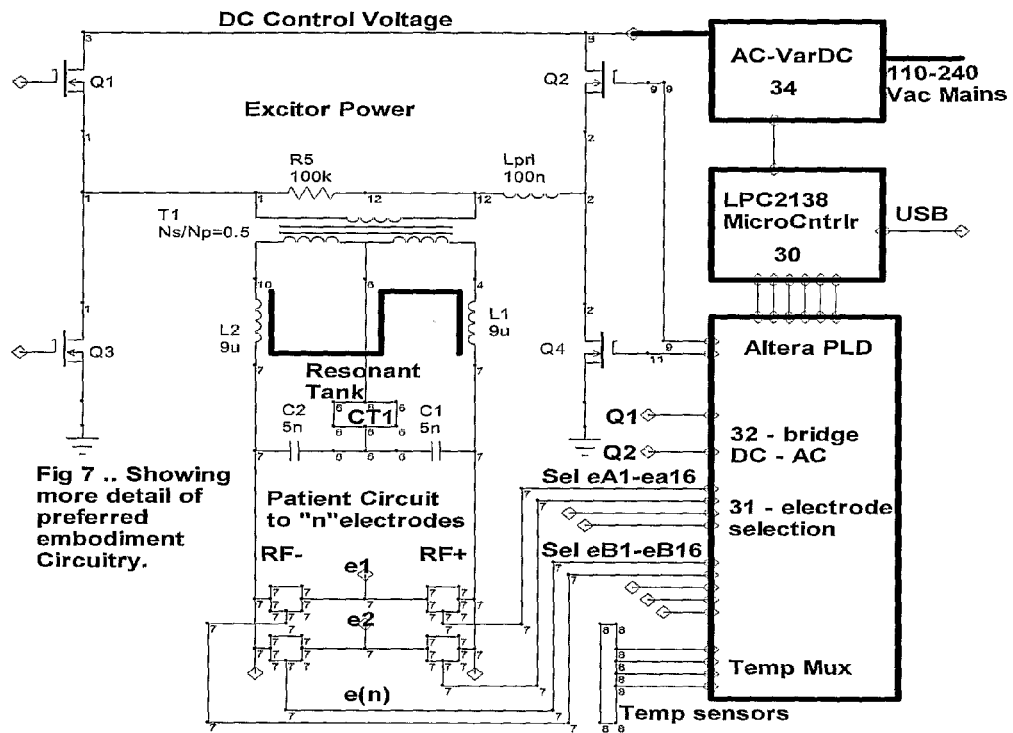
Fig 7 .. Showing more detail of preferred embodiment Circuitry.
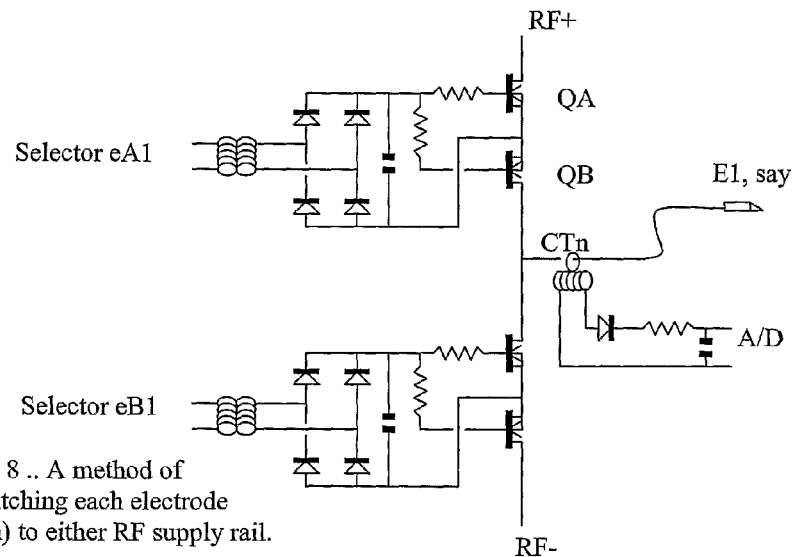
Fig 8 .. A method of switching each electrode E(n) to either RF supply rail.

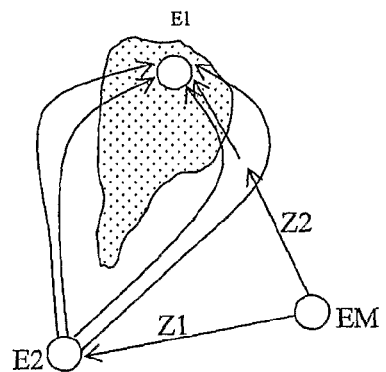
Fig 9 .. The E1-E2 current pathway gets longer as the tissue de-natures and desiccates around E1, say. The test bursts from Em monitor will detect a changing impedance between pathways shown as Z1 & Z2.
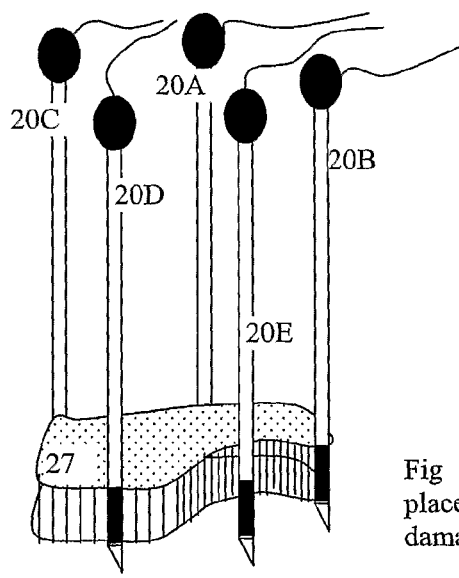
Fig 10 .. Passive electrode 20E placed to minimise tissue damage.

MINIMAL DEVICE AND METHOD FOR EFFECTING HYPERTHERMIA DERIVED ANESTHESIA

BACKGROUND

It has long been known to permanently induce anaesthesia by the cutting of afferent nerves so that the patient no longer experiences pain or other sensation from that nerve related portion of the body. However, the physical resection or cutting of nerve tissue has the propensity to create various long term medical problems including the probable creation of neuroma and the also probable permanent undesired destruction of the nerve fibre or worse, the permanent unintended destruction of adjacent fibres and still other possible undesired medical outcomes. It has been known in more recent times to temporarily induce anaesthesia for a medium term period by causing heating (hyperthermia) of the identified nerve fibre transmitting the undesired sensation. A convenient and cost effective method is the application of controlled current which causes hyperthermia by electrical resistance heating performed at such frequency that no neurological response is stimulated and that this application of energy should be done under the further limitation of temperature excursion to limit the thermal damage to the structure of the subject nerve fibre. After a period of time with the nerve tissue maintained above a certain temperature the nerve tissue is said to "desiccate" and transmission of neural signals is disabled. This desiccation process, when carefully done, is also said to "denervate" the nerve fibre but leaves intact the inherent fibre structure. The recuperative powers of the body enable this residual nerve fibre to slowly re-canalise so that after a period of time, such as 12 to 24 months, the fibre is again active. The pain sensation may then return if the original cause of the pain has not healed or been successfully treated and if so the therapy can be repeated again without permanent effect.

This hyperthermal induction of anaesthesia has hitherto been carried out by inserting the monopolar needle like probes shown in FIG. 1 through the skin of the patient using expensive low energy X-Ray fluoroscopy and an Image Intensifier to guide the placement of the probe 1. Each insulated shaft 2 of such a probe 1 carries a single electrode 3 and the probes are energised with respect to the dispersive electrode 7 (also termed a base plate, return plate, ground plate or neutral electrode). The flow of current through the body tissue is schematically illustrated by a number of arrows in FIG. 1 and it will be seen that the highest current density is immediately adjacent the electrode surface or tip 3 The intention is that the current flowing through the tissue is concentrated around the single electrode 3 sufficiently to cause hyperthermia and diverges therefrom so as to disperse or diffuse towards the dispersive electrode 7. Such tissue volumes denervated in this manner are commonly very small and so require multiple probe placements to address a volume sufficient to enclose a suitable length of the nerve fibre and its probable position. By way of example, for each of the six zygopophyseal joints needed to be treated for cervical vertebrae pain (eg whiplash injury) up to nine such separate probe placements are typically necessary. The volume and shape of the area within which the monopolar RF current is sufficient around the needle to cause adequate heating for desiccation is indeterminate in shape due to both the non-homogenous tissue structure and the non-homogeneous electrical characteristics of the tissue. When multiple such indeterminate lesions are created manually side by side, not including most probable errors of positioning, there will be included within the boundaries of the intended lesion, interstitial volumes of non-desiccated tissue as shown in FIG. 1a. The overall lesion volume is thus said to be not "integrated" meaning it is not of one tissue type where the desired tissue type was desiccated tissue.

Further, the tissue of interest to pain therapists is often transmitted by neural tissue in close proximity to ligature and to bone as well as fatty deposits in and between septa (dividing walls) such as comprises tissue around the spinal column. This is clearly non-homogenous (in contrast to heart tissue, for example, which is relatively homogenous). Similarly, the most conductive tissue in the body is that around the bone (the periosteum). Thus electrical current (and in particular monopolar current which is inherently not specifically steered or directed) is consequently concentrated in this tissue selectively in relation to other higher impedance pathways by the driving electrical potential difference. As a consequence the monopole current which was intended to be diffuse away from the monopole electrode 3 often is not diffuse but is actually concentrated in the direction of the neutral electrode. The periosteum, or bone surface tissue, is thus often the first tissue type to be desiccated. This concentration of current in the anisotropic impedance structures surrounding needle placement is of particular concern to monopolar systems which has current migration to a neutral electrode of no significant placement in regard the desired shape of the lesion. The extra electrical current which might be used to create a larger lesion is consequently distorted and attendant heating in such tissue as the periosteum may possibly cause bone necrosis to occur in underlying bone tissue. In a similar fashion higher conductive vascular pathways through the bone will concentrate current pathways and add further risk. Further, periosteum or other unintended neural tissue obliteration distal to the intended region of desiccation by monopolar electrical current en route to the distant dispersive electrode 7 is undesirable and is a reason for caution among practitioners in the positioning of the needles 1 and the limiting of the amount of power applied in complex neural anatomy.

The current practice consequently uses the small monopole needle 1 to create small cylindrical volumes of desiccation immediately around the electrode 3. The established strategy is to increase the size of the desiccated volume by making repeated needle insertions which create small side by side cylinders of desiccated tissue leaving interstitial volumes of possibly viable neural tissue. Consequently the resulting desiccated volume is not an integrated or uniform whole so the duration of the intended anaesthesia is at least indeterminate. Furthermore, this sequential activity of multiple needle placement followed by electrode activation carries risk of structural damage to the targeted nerve fibre, is extremely time consuming and consequently costly. It has been persevered with as a therapy because of the significant need of chronic pain sufferers and the advantage that needles used in FIG. 1 are able to be passed though the skin and thus the procedure experienced by the patient is not unduly invasive and is a better therapy than surgery for reasons before mentioned.

It is also known to utilise radio frequency energy in the ablation (or tissue necrosing) of heart muscle (myocardium) during open heart surgery. Here the intention is to destroy tissue which is creating or propagating irregular muscle contraction and thereby bringing about an irregular heartbeat (arrhythmia). U.S. Pat. No. 6,096,035 (Sodhi et al) discloses a needle like probe used in such open heart surgery. The procedure in practice was to insert a fixed regular array or fixed matrix of such probes into the heart muscle during open heart surgery. The volumetric density of this matrix was sufficient in its relation to the size of the pathologic neuromuscular anatomy and each electrode was utilised to detect those muscle areas which were propagating the abnormal electrical potential depolarisation signals. Once these points of functional abnormality have been detected, radio frequency energy was then applied to the same detecting electrodes and those in a suitably sized surround so as to ablate or destroy this particular muscle tissue.

This situation is schematically illustrated in FIG. 2 in which a subset of three probes 10A, 10B and 10C are shown each having three spaced apart co-axial electrodes of cylindrical configuration. These three needle probes along with many others attached to the same manifold were inserted into the myocardium (heart muscle) which is substantially homogenous. The probes 10 were arranged with a fixed regular matrix like spacing because of their mechanical construct to the manifold. In the particular situation exemplified, abnormal electrical signals were detected from the electrodes in a "sensing" mode when no energy was being discharged by the device in the tissue.

As a consequence, when a radio frequency voltage was applied in a bipolar fashion sequentially activating all these electrodes, a portion of tissue was ablated or destroyed. No attempt was made to design or predetermine the shape of destroyed portion save to have it larger than the detected pathologic tissue.

The above described prior art application in relation to cardiac tissue is substantially different from the field of activity of the present invention in that, firstly open heart surgery is involved compared to a percutaneous acupuncture like insertion of needles in the field of the present invention. Secondly, the pathologic heart muscle tissue is intended to be ablated or destroyed then over time replaced with correctly functioning tissue whereas such tissue targeted by the subject device and means alters the nature of correctly functioning tissue and allows it to return to the same correctly functioning state subsequent to the period of anaesthesia. Thirdly, because the heart muscle itself generates electrical signals which move through such muscle tissue as a wavefront, it is not necessary or desirable for the needle like probes 10 to be positioned with demanding accuracy as in a comparative sense there are no neighbouring tissue structures which must be protected. This is because there is a sufficient density of probes and a sufficient number of electrodes in this fixed matrix arrangement for the defective region of muscular tissue to be electrically detected and then upon mechanical rearrangement of connections, be ablated.

Additionally no dynamic adaptation of the discharge pattern was undertaken nor are there any electrodes left out of what was determined to be the active set and indeed the only set to be activated for discharge of energy. The therapy was different and consequently the device contrived to provide such therapy was different.

U.S. Pat. No. 5,383,917 (Desai) discloses an alternative prior art technique involving ablation of heart muscle by passing a catheter including electrodes through a vein or artery and into the heart. Here the tissue to be ablated is immediately under the surface of the heart muscle (the endocardium). Although not as invasive as open heart surgery, the intention is to disable aberrant depolarisation pathways in the heart muscle underlying the placement of the electrodes. In such therapy the puncturing of the endocardium is not desirable given it would have to be done in the actively pumping and mobile heart wall. Again the tissue to be destroyed by ablation is substantially homogeneous. Furthermore, similarly, it is intended to cause destruction of the ablated tissue such that regrowth will replace it with correctly functioning tissue.

In inventions for the cardiac muscle ablation using RF energy and tumour tissue ablation where the shape of the ablated tissue volume is not intended to be controlled with any precision, it being intended that such volume simply contain the volume of pathologic tissue which is intended to be necrosed. Further, such ablation procedures do not usually need control of temperature and it is common to have the temperature uncontrolled which commonly exceeds 100 deg C. so creating vapour which transiently generates gaseous voids in the tissue. Such permanent necrosis and subsequent absorption by the body is undesirable for the purpose of neural anaesthesia. The fragile nature of the threadlike nerve fibres would be damaged by the explosive creation of vapour and the physical structure of the fibre is intended to be preserved for the re-establishment of the neural pathway and thus no resorption is desired.

In the case of myocardial tissue it is aberrant muscle tissue being ablated which is generating arrhythmias in heart muscle by circus loop depolarisation or as another example terminating fragmentary conduction across the AV septa which is in both instances pathologic tissue and in neither case is intended to revert to a conductive state. Whereas with the desiccation of neural fibre the neural fibre is usually not of pathologic tissue, but is transmitting undesired signals to the spinal column.

SUMMARY OF THE INVENTION

In contrast to the aforementioned monopolar needle and its requirement for multiple manual placement and "burn" application cycles which are extremely time consuming and costly it was intended to develop a Device which could perform the entire therapy for one section of nerve fibre with ONE so called "burn" activation. The principle virtue of such an approach is that fewer punctures are needed and the procedure takes less time thus is more conducive to the comfort of patient. The secondary benefit is that with fewer punctures made with greater separation from the fibre position there is less chance of physical damage to the fibre itself. The third benefit is that the lesion has a far more integrated nature leaving less potentially viable interstitial tissue and consequently greater predictability of the outcome being medium term anaesthesia.

There are two principle effective features of this invention that determine its efficacy. The first is that the size and shape of the lesion it can create is dependant on the density with which electrodes are placed surrounding the volume of the desired lesion which is placed to contain the traverse of the target nerve fibre. The second is the manner electrodes are activated in dynamically selected sets of active discharge electrodes which are selected by a control process during the creation of the lesion. The deployed electrodes are able to provide current attached to either of the two RF power ports, or polarities, from the RF generator and are thus able to be switched in and out of a variety of active discharge patterns during said single activation. It must be noted that the term "polarity" is used in the instantaneous sense and that it is perhaps easier to consider this characteristic of the electrodes as meaning that any electrode can be made to discharge energy to any other electrode in the deployment and thus any electrode in a deployment may be made isopotential with any single other electrode or any other single group of electrodes in the deployment. Each of the deployed electrodes is also able to be switched with such momentary action that no hyperthermal effects are created thus allowing some selected electrodes to effectively "sample" a diversion of current from any actively discharging set of electrodes while such discharge is in progress. This momentary diversion may be made to either RF rail or otherwise stated, to either isopotential group of the opposing polarities of the selected set activated for discharge of energy into the tissue.

The objective of the momentary activation of electrodes is to monitor the coagulum build up on the active electrodes. As the therapy proceeds, such differential buildup occurs due to the in-homogeneity of the target tissue and if not compensated for will lead to some electrodes becoming "isolated" by relatively non-conductive coagulum or semi-desiccated gunk. The FIG. 9 addresses the geometry of such phenomena and illustrates the manner the impedance changes can be indirectly determined between the two active electrodes in this example. In FIG. 9 the E1-E2 current pathway gets longer as the tissue de-natures and desiccates around E1, say. The test bursts from Em monitor will detect a changing impedance between pathways shown as Z1 & Z2. A control response is thus to reduce current to E1 and involve E2 in more pathways at perhaps different energy levels. Such a valid alternative is to include Em and E1 as one polarity returning to E2. The current density is thus intensified on E2 and reduced on E1. The reconnection of electrodes is a response of the control system as is the energy delivered to electrodes with the known parameter of what current density is appropriate for each electrode size to create temperature/desiccation—which is measured in terms of effective change in impedance during an activation.

This FIG. 9 also demonstrates the significant advantage of using multiple electrodes to achieve uniform distribution of coagulum between the needles of the deployment, as is generally the case the electrode Em is a monitor electrode for some succession of electrode discharge sets and is an active discharge electrode in other discharge patterns.

While specific therapies had been the initial objective, application of the Invention has the capability to produce arbitrary lesions by having an available standard set of 16 available electrodes and a further 5 channels of temperature. As such, the number of electrodes needed for known procedures is usually less than available.

As is inferred by the more general case than illustrated in FIG. 9, included in a therapeutic deployment of electrodes is a subset of electrodes each of which may optionally act as a monitoring electrode used in momentary activation only for the sole purpose of monitoring current distribution in the associated deployment. Such electrodes are usually selected on the basis of their being physically located suitably to "see" with suitable relationship to each set or electrode they are to monitor. As an example, FIG. 5 shows that each electrode can in turn be used to monitor the discharge of any other pair, also to monitor the discharge of another pair toward one single electrode.

Further toward the objective of being able to place edges of lesions close to critical anatomy some electrodes are also able to be delegated to the sole purpose of monitoring where they can ensure no current density in their environment is able to produce hyperthermal effects. Such a "monitor" electrode can also use a temperature sensor stylet. Such a monitor electrode is placed at critical anatomy where no thermal damage can be permitted allowing close edges of the thermal lesion to such critical tissue.

While the deployed electrode array has elements performing various programmable tasks as above, the RF generator shown in FIG. 3 outputs energy to the array continuously according to the contrived natural regulation of the resonant power output stage 4 which is never overtly switched off during sequential selection of activated pole pairs or sets in the deployment, including the functions of the electrodes used for momentary activation. At a slower supervisory level, effected by the controller 1 the overall generator performs an overt and continuous control using feedback from said momentary activation current signals or temperature sensing functions of said probes and switching connections to achieve evenly distributed hyperthermal temperature by way of controlled RF current distribution among the electrodes in the deployed array, and thus ultimately determines the uniform integration of the lesion, the end point of energy delivery, and a predictable anaesthetic effect.

The present invention is intended to comprise both a method and apparatus whereby the form of the lesion created by desiccation can be closely controlled. It is highly desirable to control the shape and size, for example, of the desiccated volume because the period for which anaesthesia is induced has a dependency on the desiccated length of the nerve tissue. It is also a restriction on the lesion that it be placed in and around complex anatomy of bone, tendon and a variety of cartilage and other fatty and muscle tissue. In order to navigate the boundaries of such a thermal lesion placement it is advantageous that the device have special parts and function provided to be used for the preservation of critical fibres and structures at the boundary of the intended hyperthermal lesion.

In accordance with a first aspect of the present invention there is disclosed method of inducing medium term anaesthesia in mammals by radio frequency desiccation of elongate nerve tissue, said method comprising the steps of:

(i) inserting into a mammal a selectable plurality of electrodes that are mounted on probes characterised for specific nerve anatomy each having at least one electrode and an electrically conductive lead extending therefrom, (ii) selecting the orientation and degree of insertion of said probes to define by the electrodes of said probes a volume containing at least a substantial portion of said elongate nerve tissue but which can be bounded by electrodes excluding other tissue from hyperthermic effects, and (iii) applying a controlled distribution of average radio frequency current between pairs or sets of said electrodes to heat, to the extent of effective desiccation as measured by distributed measurement of temperature, said volume, and (iv) altering the manner of discharge between electrodes by adaptation of the discharge sets producing the hyperthermic effects.

In accordance with a second aspect of the present invention there is disclosed a device which uses an RF resonant tank circuit as an output stage which supplies RF current to a plurality of electrodes arranged as pole pairs or sets which connects the tissue in which they are therapeutically deployed as the damping element of such oscillation and so offers an energy output profile against said tissue denaturation which is advantageous in that such time required to desiccate the target volume of tissue is minimised in addition to the aspects of high efficiency of energy usage and consequential miniaturisation of the device.

In accordance with a third aspect of the present invention there is disclosed a device which has said resonating tank circuit connected to said plurality of electrodes via a selector matrix which can connect each electrode to either resonance output port polarity achieving a therapeutic and dynamically alterable set of electrodes arranged in pole pairs and other sets such that a Radio Frequency heating current pattern is produced across the said strategic deployment of electrodes which is an adapted response to measured differential current densities and temperature measurements over the period of device activation accommodating tissue non-homogeneity and creating an adequate and suitably integrated thermal lesion for therapeutic purpose of neural de-activation.

In accordance with a fourth aspect of the present invention there is disclosed a method of supplying RF electrical power to a network formed by plurality of electrodes each of which is inserted into tissue of a mammal, said method comprising the steps of:

(i) energising in sequence dynamically alterable pairs and sets of said electrodes as determined by a supervisory control function at a high frequency of selection, and (ii) continuously monitoring the impedance and particularly its distribution between at least ONE active electrode pair in a deployment with other active or monitoring function electrodes, which may or may not also be used alternately for energy delivery or sensing changing impedance balance between other activated electrodes or also by direct temperature measurement.

The subject device and its minimal circuit embodiment is shown diagrammatically in FIG. 3 representing a block diagram shown in elaboration by FIG. 4 a circuit wherein the tissue impedance itself is an inherent part of the resonant device.

The tissue impedance changes over the period required for desiccation of each bipolar pair or set current pattern distribution and is in addition markedly different from one activated electrode bi-pole pair or set to another. Given the damping function of the tissue the output adjusts to deliver an optimum for purpose power versus tissue impedance profile from one set to another without any involvement of the processor control function to adjust either current or voltage. Further, the designed output impedance of the resonant tank circuit overcomes incidental reactance of electrodes and lead dressing and connections. A salient feature of the implied simplicity of the second aspect is that the consequent speed of selection/de-selection of bipolar set arrangements among the electrodes can be done with so few components and at such speeds as allow large electrode populations to be deployed and activated in arbitrary sets which can have the currents and voltages of the deployment sampled with a high sensitivity commensurate with resonant parameters where the "Q" of the resonant circuit is highly sensitive to impedance changes in the network and yet the noise is low because of the highly selective bandwidth.

As shown in FIG. 3 the AC to DC function supplies a variable DC voltage which is impressed on the "excitor" functional block 2. This DC voltage is the ultimate and sole determinant of the output power limit of the resonant circuit block 4 shown to be in parallel with the entire electrode array.

The momentary activation phase for a variety of electrodes in a deployment is further used to test the perfusion stability of a lesion immediately following the discharge of energy phase. This is done over larger periods than normally used for active discharge and inflicts no discomfort on the patient. If such impedances as represent tissue desiccation are not static then it is surmised that electrolytes are re-perfusing the lesion and further activation of discharge may be contemplated. The endpoint of the lesion creation process is considered to be when minimal alteration occurs in the current balance by as assessed by the monitor electrodes performing as discussed above. The controller and display block of FIG. 3 shows an image of the instantaneous distribution of current in the array in addition to emphasis on areas of current density which are changing throughout the strategically spatially sampled volume as is commonly displayed in simple electrical impedance tomography which can be used as one guide to operation in a display presentation to determine the end point of the energy delivery to achieve the desired denervation result.

BRIEF DESCRIPTION OF THE DRAWINGS

A preferred embodiment of the present invention will now be described with reference to the accompanying drawings in which:

FIG. 1 is a schematic representation of the prior art apparatus used in nerve desiccation including a small cross-sectional view of the effects of manually repeated activations, FIG. 2 is a schematic representation of the prior art apparatus used in ablation of cardiac muscle (myocardium), FIG. 3 is a block diagram of the subject device showing major functional sections, FIG. 4 is a diagrammatic representation of the minimal output stage allowing such high efficiencies as 95% and wherein the tissue is shown to be an inherent part of the device resonant circuitry.

FIG. 5 is a schematic representation of a simple possible probe arrangement in accordance with the preferred embodiment where it is to be shown that ALL combinations of electrode patterns are able to be activated, FIG. 6($a$) is a graph demonstrating the essential features of self regulation including power limitation approaching short circuit, maximum power at maximum rate of denaturation of tissue and limiting power at onset of tissue desiccation and other high impedances such as transient switching disturbance.

FIG. 6($b$) more closely details the circuit behaviour at short circuit and also demonstrates the self regulation of the current waveform. A range of curves exist for behaviours of power regulation and current regulation for a limited range of frequency disparity between the resonant frequency of the output tank circuit and the excitor frequency. Generally current regulation is sacrificed for better power regulation. The power curves of 6($a$) which exemplify power regulation characteristics as suitable for the purpose of desiccating tissue have a larger such disparity than the current regulation shown in 6($b$).

FIG. 6($c$) demonstrates the resonance effect on Voltage when the circuit is parameterised for constant current as in 6($b$).

FIG. 7 is a schematic circuit diagram of the radio frequency generator of the preferred embodiment, FIG. 8 is a schematic circuit diagram of an individual electrode switch FIG. 9 is an equivalent circuit diagram for 3 electrodes, and FIG. 10 is a view similar to FIG. 3 but of a different probe arrangement demonstrating the boundary probe function.

DETAILED DESCRIPTION OF THE INVENTION

In FIGS. 3 & 4 the minimal design is diagrammatically shown. No vulnerable to failure active semiconductor is used in the isolated patient circuit section shown which is passive in its regulation by the minimal component RF exitor circuit driving the primary side of the isolation transformer. The only active parts in the isolated power delivery section (the patient circuit) comprise the low power (less than 100 mW) switching and passive monitoring devices shown in FIG. 10. Further, the monitoring function of other deployed electrodes will discern faulty switching mechanisms when in operation.

The natural and uncompensated regulation curves, meaning regulation achieved without feedback control, are shown in FIGS. 6($a$),($b$),($c$) which are derived from the circuitry shown in FIG. 7 where it can be seen that at short circuit the RF current is limited and over the range of tissue impedance power is delivered by virtue of the nature of the excitor circuit and resonant LC tank circuit phase inter-action. Given a fixed phase and amplitude at the excitor output port, an excess current thru the transformer and series resonant tank circuitry reduces disproportionately the voltage amplitude available at the tissue impedance. A further graph 6(c) is shown indicating the current regulation capacity of the circuit and includes short circuit. The degree of non-linearity of the Power Vs tissue impedance is largely determined by the separation of excitor frequency and the natural frequency of the resonating tank circuit.

Such boundary condition of limited power dissipated at short circuit impedances between the electrodes is highly desirable to avoid momentary tissue carbonisation (when electrodes are inadvertently shorted) such as might happen if overt microprocessor control were necessary with associated delays in regulation. It is also to be noted that at high tissue impedances, which represent desiccated tissue, the energy output is relatively constant. This is a unique and desirable property of the resonant LC output stage in this embodiment. It is further noted in these natural regulation curves 6(a) that the maximum power output occurs between 200 and 450 ohms which is suited to the impedance of tissue in the early stages of cellular denaturation and excretion of cytoplasm conducive to convection and transport of heat between the electrodes. Such a regulation curve commencing at lower energy and proceeding to maximum output power in this region of maximum liquid convection and conduction effects which are prevalent at the time of maximal cytoplasm excretion in the target tissue volume ensures better lesion integration and faster lesion creation. At the time of maximal convection the temperature distribution is also most uniform which is the optimum period to be depositing the maximum energy in the tissue. Of collateral significance the rates of change of tissue impedances around the electrodes in this impedance range is maximal thus allowing greater sensitivity of the method herein and below described of determining the distribution of impedance throughout the said spatial network of electrodes.

The application of feedback to "flatten" such natural regulation curves by adjustment of the excitor waveform as shown is held as not desirable and in the embodiment herein is applied minimally. Such restriction of highly accurate constant power over the impedance range (a flat curve) is not efficacious given the advantageous characteristics of the output power versus load (resistance) of this embodiment of resonant LC tissue desiccator/oscillator as described herein. It is also emphasised that the reduction in the time taken for delivery of the therapy is a critical factor due to the usual discomfort of the patient undergoing such therapy and consequently such regulation curves are considered optimal in nature and a salient feature of this invention.

Turning now to FIG. 5, in accordance with an explanatory embodiment of the present invention, four needle like probes 20A, 20B, 20C and 20D are used. These needles have an insulated shaft, and a single electrode tip which is connected to a corresponding conductive lead 24. In FIG. 5 the four probes 20 are shown inserted into tissue lying immediately adjacent a nerve 25 which is generally transverse to the direction of insertion of the probes.

It will be appreciated from FIG. 5 that since each of the electrode tips 20 has an appreciable longitudinal extent, the four electrodes as placed define a thin, generally elongated volume 27 indicated by broken lines in FIG. 5 which has a thickness which is comparable to, and determined by, the longitudinal extent of the electrode tips. The location of the probes 20 and their depth of insertion are arranged so that the volume 27 closely follows the course of the nerve 25 and may be on, or closely adjacent to, a bone surface.

Rather than energise the probes 20 in monopole fashion as indicated in FIG. 1, the probes 20 are energised in bipolar fashion so that each of the six pairs of equal area electrodes 20A/20B, 20B/20D, 20D/20C, 20C/20A, 20A/20D and 20B/20C are energised in turn. Additionally the electrodes can have alternate management of current density surrounding each electrode by opposing ONE electrode with any other TWO, so electrode 20B can oppose 20C+20D where the current density on the electrodes C & D are halved in relation to the current density on 20B at whatever power level occurs on the regulation locus. AU combinations of electrodes can be "activated" thus 6 of 2 or pairs, 4 of 2 to 1, and 4 of 3 to 1 discharge "sets" are available. AU patterns may be activated with different power levels.

This assumes that the tissue is somewhat homogenous however if not subsequent adaptations of electrode pattern will be produced to create equally high impedance over the entire volume. In this way the entire volume 27 is inherently covered by a plethora of possible current pathways, however the strategies to achieve this homogeneous lesion needs be highly adaptive and optimised by additional control means to determine the end point of energy delivery.

In the simplest example, RF current is made to pass between electrodes 20A and 20B in the first instance and similarly through each of the other five pairs in turn in a manner which may be termed sequential bi-polar excitation. For reason of reducing the time of power application it is also possible to activate two pairs, say 20A-20B and 20C-20A simultaneously, or also 20A-20B/C or 20B-20A/C/D. This may be consequent to the control algorithms below mentioned determining that current density of needles A or B need be in a region of x2 current density or x3 the minimum current density for some period of time. As coagulum builds up around an electrode it is necessary to monitor the changes occurring throughout the lesion and utilise algorithms dependent on sensory mechanisms provided by this device by way of momentary activation of electrodes as discussed previous.

The energy delivery control algorithms ensure:
(i) Each needle does not asymmetrically accumulate coagulum with respect to others in this network of electrodes to the point it is of high impedance and unusable for further energy delivery.
(ii) Each current pathway is monitored by a third inactive electrode which can detect the impedance changes between the active electrodes by momentarily sampling its own impedance path value to each of these active electrodes. In overview terms each electrode in the deployment can also act as a sensor of the distribution of tissue impedance which determines current distribution and attendant heat production.
(iii) The degree of homogeneity in an adequately desiccated lesion is an indication that viable tissue may or may not remain between pathways. Of significant benefit assisting lesion integration is the fact that as tissue desiccates its impedance increases—leaving lower impedance pathways attracting higher current density which facilitates lesion integration and end-point homogeneity.
(iv) The end point of energy delivery will occur when such monitoring electrodes determine minimum change of distributed impedance for a number of activation sequences—such impedance will have reached a maximum and remain unchanged within programmed criteria.

(v) According to heurism and mathematics in any medium such lesion integration, homogeneity and definition will only be made with a requisite density of electrodes.

(vi) The monitoring electrodes perform a crucial part of the procedure after the energy delivery is considered complete according to (iv) above, by sampling and detecting impedance changes indicating instability of the thermal lesion. This procedure takes a short while, with no sensation felt by the patient, and such undesired changes in impedance post activation would indicate a limited anaesthetic period caused by reperfusion of the intended thermal lesion. Extension of the activation process is then countenanced.

Turning now to FIG. 7, from the schematic circuit diagram of the radio frequency generator of approximately 30 W power, it will be seen that a microcontroller 30 is connected to, and controls the operation of, a multiplexer programmed into a programmable Logic Device 31, a lagging phase full bridge controller 32, and the variable voltage DC supply 34 also controlled by the microcontroller 30. The variable control voltage supply 34 determines the DC Voltage applied to the full bridge activated electrode set and is applied to a full bridge circuit formed by four MOSFETs Q1-Q4 which are connected to the primary winding of a transformer T1 which has a centre tapped secondary winding. The full bridge circuit has monitoring of the DC voltage applied across it and also the primary current. The patient circuit monitors the current in C1 and C2 by current transformer which indirectly is a measure of the output patient circuit voltage. The full bridge circuit acts as an exciter energy source for the resonating parallel LC tank circuit. Each of the secondary windings passes through two windings of mutually coupled inductors L1 and L2 respectively to each of two capacitors C1 and C2 which are connected in series and equal in capacitance. The centre point of the capacitors is connected to the centre tapping of the secondary winding via a high isolation current transformer CT1, the output of which is connected to the phase controller 32. The capacitors C1 and C2 together with the entire inductance constituted by the self inductance of transformer T1 and the coupled inductors L1 and L2 constitute a resonant tank circuit of a specific resonant "quality" termed "Q" which is damped by further parallel resistance represented by the tissue enclosed by the activated bipolar electrode pairs or sets. The frequency of oscillation of the exciter generator, preferably approximately 490 kHz, is determined by the set frequency of the exciter controller of the full bridge circuit. The natural resonant frequency of the resonant tank circuit is designed to be close to, but not equal to, this exciter energy feed frequency. At specific settings of the frequency difference between exciter and resonator the changing tissue impedance during desiccation reflects greater or lesser current through the coupled inductors which represent a complex impedance such that for example, greater current drawn by the load provides less output voltage and lesser current provides greater output voltage given the voltage over the full bridge has been set to a constant value known to be commensurate with an output regulation of power locus such as shown in 6(a). As is expected at other settings close to resonance, as the load impedance increases the resonant voltage also increases which also results in a form of current regulation shown in graph 6(b). An example of the resonant voltage curves is shown in 6(c). In simpler terms the manner this circuit regulates output power (it being proportional to Vrms multiplied by Irms) is where, increasing current across the coupled inductors is reflected to the primary of the transformer T1 as a phase lag which then draws more current from the fixed frequency exciter oscillation. By design the phase relationship can ensure limited current at zero impedance 6(b) and such other desirable power output regulation characteristics as described herein. Such a circuit provides a family of curves and characteristics depending principally on the relation between the excitor frequency and the resonant output frequency. The circuit is able to dynamically alter the frequency of the excitor stage or to increase or decrease energy supplied to the resonating tank by Pulse shaping options which could be supplied by transformer CT1 which determines the "flatness" of curves of FIG. 6(a) if required. Such manipulations are able to be performed by the Microcontroller in concert with the PLD device in the preferred embodiment but it seems not to be advantageous.

The sole control of output power is set by the output voltage from the variable output voltage AC to DC Power factor controller (34) which is set a priori with the voltage commensurate with the desired output power level, or regulation curve for the therapy. At high impedances large circulating currents occur in the excitor bridge as the resonant current needed to activate the capacitors in the resonant tank circuit are alternately charged and discharged of voltage at high frequency. Such currents are largely conducive to Zero Voltage switching of the excitor bridge switching FETs—a situation highly desirable for reliability and efficiency. Such high currents as are circulating are reactive and returned to the DC driving voltage output.

This circuit has an efficiency only limited to a practical degree by the magnetisation power loss in the inductors and transformer, consequently achieving such high efficiency as 95%. Hitherto efficiencies of devices using "Class AB" amplifier output stages for RF ablation are generally 50%. for the output stages alone. The dissipation of this energy loss needs large heat sinking and packaging and less than optimal reliability due to the necessary use of power semiconductors in linear mode.

This subject embodiment circuit of FIG. 7 can be thus seen to provide the natural regulation that allows fast switching between electrode bipolar pairs or sets that have different impedances, it not being necessary to switch off the continuous wave output of the resonating tank circuit provided a limiting damping resistance is applied in parallel with the resonant tank circuit which otherwise theoretically approaches infinity at open circuit or other damping dissipative load, but which in practice does not due to natural circuit element parasitic losses. Any loading by tissue causes immediate reversion to the regulation curve locus at a "power out" position dependent on the load impedance value.

The features combined of high efficiency, minimal parts count, minimum active parts, no linear active parts, high isolation to patient circuit and attributable in part to the natural self regulation properties of the circuitry allow the device to be embodied in a small sterilisable package and used conveniently as a small medical instrument.

In further explanation of the circuit in FIG. 7, each of the capacitors C2 and C1 is connected via a corresponding switch eA1 and eB1 respectively each of which is joined to a corresponding electrode E1 shown in more detail in FIG. 8. The system can have any number of electrodes but is typically sixteen. As a consequence of this arrangement, each pair of electrodes (eg E1-E2; E1-E3; . . . , E1-En; etc) is able to be energised in two ways. For example, the pair of electrodes E1 and E2 can be energised by turning on the switches eA1 and eB2 or by turning on switches eA2 and eB1. In general the microcontroller will sequentially energise all pairs or sets of electrodes in a deployment in a time period referred to herein as a "frame Period". Each electrode pair or set is available for activation for an equal period inside this frame Period such that each electrode bipolar pair or set has a maximum activation time equal to the frame Time divided by the number of electrode pairs or sets to be activated each frame period. This activation period available to each electrode pair or set is commonly referred to as the PWM period and such is the control that within this PWM period the electrodes are activated with a "duty cycle" such that relative energy delivery between electrode pairs or sets is controlled as determined in assessment by the control algorithms as to the need or not of energy to create an integrated lesion of the desired form. As pairs or sets enter desiccation and are dropped out of the sequence or sets get larger for simultaneous activation, the frame period will not be constant.

In this particular embodiment, each probe (for example probe 20A in FIG. 5) has a single common sized electrode and thus the number of electrodes and probes are equal. In the general case and for other desired thermal lesions electrodes need not be common sized nor need there be equal numbers of electrodes on probes. The equivalent circuit in this example formed between each pair of electrodes is indicated schematically in FIG. 5 and appears to the system to be a resistance connected in parallel to the output port of the Resonator Circuit. Irrespective of small parasitics of leads, selector switches etc and connections the inter-electrode impedance is predominantly resistive and NOT reactive.

As seen in FIG. 8, each of the probe switches eA(n), eB(n) is formed from two series connected FETs—QA and QB. A signal transformer Tn has its primary winding supplied by the selector 31 and its secondary winding is connected to a signal diode bridge. The output of the diode bridge is connected to the gate of each of the FETs QA and QB such that a resistor dumps gate charge to quickly terminate gate ON charge and the remaining resistor avoids gate circuit coupling at switch on threshold between FETs QA and QB. Other means of effecting the power switching are available to those skilled in the art and such function is recognised as that of a solid state Relay and may involve photovoltaic isolation.

In order to provide an indication of the current flowing through the switch QA-QB, a corresponding current transformer CTn seen in FIG. 8 is provided which has its secondary winding output rectified by diode bridge DBn and passed through a low pass filter in the form of a capacitor and resistor C, R. The output of the low pass filter is in turn provided to the Microcontroller Analog to digital signal converter for quantitative measurement and monitoring of the current. Thus all electrodes have their RF current monitored, a necessary parameter for the measurement and control of the distributed currents in the desired lesion.

It follows from the above circuits that each of the electrodes E1 ... En can be used in either one of two ways. The first way is in an energising mode in which pairs of electrodes are energised by the RF current. This energy discharge causes tissue to coagulate preferentially around certain electrodes in preference to others. This distribution of coagulum on the electrodes is not uniform because the tissue and its perfusion is not uniform as stated. This leads to the second function of the similar electrodes which is to monitor the progress of the desiccation and, in particular, the build up of coagulum. This will be explained in particular with reference to FIG. 9 where only three electrodes E1, E2 and Em are illustrated. The impedance between the electrodes E1 and E2 varies as the energy is dissipated by the tissue between them. Eventually, due to non-uniform perfusion and other factors, one electrode, say E1 in this example will build up a volume of coagulum as represented by the shaded area.

If the tissue between electrodes E1 and E2 is energised, then impedance between E1-E2 increases over time as the desiccation proceeds (typically from 100 ohms to 2000 ohms but dependent on perfusion, type of tissue, hydration and electrode size). Concurrent with the energisation of E1-E2, one of the two switches connecting Em to either RF power supply rail as shown previous is momentarily activated. This means that Em will be at equipotential with say, E2, and thus the current to E1 will be shared between E1 and Em. The difference in current drawn by Em when compared to its reading when activated to the second RF rail, say E1, will be reflective of the impedance around each electrode. The manner such an indirect impedance measurement changes is a sensitive monitor of the build up of coagulum and a demonstration that three electrodes can achieve better lesion integration than two electrodes and four will improve it further. It is implied that the initially referred to electrode Em will also be used to discharge energy and in a symmetrical fashion E1 & E2 will in turn be monitoring electrodes.

As a consequence, in order to provide a more uniformly desiccated lesion in an electrode deployment of say 4, the electrodes pairs including electrode E1 would be energised less and electrode pairs including electrode E2 would be energised for a longer period of time in the manner Pulse width Modulation can regulate energy delivery or by dropping pairs or sets from the activation sequence. The general intention of this method being to form coagulum and later desiccated tissue approximately equally on all the electrodes being energised and the spaces between so as to form a relatively uniform lesion which extends over an entire volume defined by the spatial arrangement, density and number of electrodes, each as arbitrarily determined for specific therapy by the clinician or according to configure files for recognised or routine therapies utilising standardised numbers of electrodes, types of electrodes and associated probes and standardised approximate placements of same electrodes and probes in tissue.

Turning now to FIG. 10, a variation on the situation illustrated in FIG. 3 is illustrated. Here an additional probe 20E is provided. This additional probe 20E is inserted at some critical area where no hyperthermia effects are desired. This "boundary" electrode 20E can allow close causation of a thermal lesion but is never itself part of an activated pair (other than momentarily sampling surrounding currents, or if containing a thermometry device only providing such monitoring as required for the method). This insertion of probe 20E can be carefully performed under the abovementioned X-Ray and Image intensifier control and is specifically intended to preserve tissue close to critical anatomy such as efferent and other afferent fibres or ligature and bone or cartilage structures while ensuring the desired lesion boundary to be as close as possible depending on the density of the arbitrary placement of electrodes. This also provides safety and the remaining probes 20A-20D which are deemed needed to be inserted may require less precision and caution as to their placement. It is also be generally common knowledge that high energy activations of electrodes produce smaller lesions than lower energy longer term activations. This is also a controlled factor applied to the other pairs or sets when determining the control strategy when using such a boundary control electrode as 20E.

Since no lesion is required at the position of electrode 20E, this electrode is never activated to create hyperthermia in its immediately surrounding tissue. It is however energised momentarily in monitoring mode with selected other electrodes and hence discharges such little energy that no coagulum forms on the electrode of probe 20E. Instead, the probe 20E is used, in particular, to monitor the build up of coagulum on electrodes 20B and 20D. In this way, the energisation can proceed so that the electrode pairs 20A-20C and 20A-20B and 20C-20D are energised preferentially and that the electrode pair 20B-20D is energised only to the extent that electrode 20E detects no current density indicative of hyperthermia creation considering its resistive isolation to either monitored and intended active pair or set when sensed current is assessed to both polarities of excitation which in effect measures the impedance of a parallel path between activated pairs. Electrode 20E is additionally activated only momentarily for the purpose of sampling current distribution and impedance as appropriate for pairs such as 20A-20C and in this while discharging so little energy in the tissue that no hyperthermia is caused. Alternately or concurrently, a temperature probe can be used at position 20E. The result is that the resulting lesion 127 does not extend towards probe 20E but an environment of viable and unaffected tissue around probe 20E and beyond is maintained. In this way not only can a lesion of approximately uniform consistency be created, but the shape of the lesion can be better determined. The complexity of the shape of the volume 127 is dependent on the density of the electrode placement according to spatial sampling principles.

A communication pathway exists between the RF generator control 30 and a laptop or other computer such that configuration files and other configuration and therapy relevant information can be displayed, stored and downloaded into the controller 30. This is not a critical function in terms of the therapy delivery and default config files can be loaded to non-volatile memory for semi permanent storage inside controller 30 such that it can be used for a limited number of pre-configured therapies without the communication interface being active. However such monitoring as allowed by the connected PC if desired collects treatment records and has numerous safety warning and imaging functionalities.

The foregoing describes only one embodiment of the present invention and modifications obvious to those used skilled in the biomedical or electronic arts, can be made thereto without departing from the scope of the present invention. For example, the probes can each be provided with a thermal detector such as a thermocouple or thermistor so as to monitor the temperature of the region being desiccated.

Similarly, the probes can be provided with more than one electrode so that greater lesion thickness and a deeper or more longitudinal dimensional aspect in the direction of probe penetration to the lesion can be achieved. Further the electrodes need NOT be of uniform size while subject to control of coagulum build up as herein. For example a larger electrode can be included in a bigger set of opposition polarity smaller electrodes to decrease the period required for desiccation. In the setup of the control such parameters as electrode sizes are significant factors of the subject control process and the complexity of the desired thermal lesion shape will determine the electrode surface areas and surface current density and plurality of same.

Furthermore, the impedance between any, and all, pairs of electrodes is measured at some time interval after the initial desiccation process is terminated. If the impedance drops during this examination period, say below 1000 ohms, this indicates reperfusion is effective and that the lesion has access to electrolytes and nutrients which may indicate a faster recovery of the nerve fibre and its immediate surrounding tissue. If so, the network of electrodes can be re-activated to discharge energy in the same manner as before to create a more stable lesion. This process is continued until a suitably low reperfusion rate is achieved. It is known that for some applications the probes are hollow cannulas, and chemicals such as anaesthetic or other therapeutic or ablative fluids are used without need for any change in the functionality of the embodiment herein described where such cannulas have one or two or more electrode surfaces associated with such probes. Use of such a probe as 20E above for both anaesthetic chemical delivery and thermal or current monitoring is common and advantageous.

In such routine placements as mentioned herein when a configuration file is well developed the probes needed for the specific therapy can each be mechanically attached to a manifold or formwork construction such that simultaneous placement is done with needles in a fixed spatial arrangement suitable for a specific anatomical presentation thus further automating the therapy to achieve increased safety and lower cost.

Further, alternate probe construction may allow the placement in tissue of detachable electrodes which have flexible electrical leads withdrawing from the parent cannula making connection between the RF generator with its component parts as herein and said electrodes which are placed with the same spatial density paradigm for lesion design as otherwise described. Such construction allows electrode placement in mobile musculature and skeletal parts indicated for anaesthesia.

The embodiment described herein significantly improves clinical electro-anaesthesia procedures by:
1. Improving quality and predictability of anaesthetised period by reducing indeterminacy caused by making successive manual placements in relation to the anatomy and memorised previous placements.
2. Reducing the period of time required to perform such therapies which is of benefit to fluoroscopy theatres and clinicians managing an existing excessive case load.
3. Reducing the discomfort for the chronic pain suffering patient by reducing the period required for the therapy
4. Reducing the instance of physical damage to the fibre by desiccating a larger volume of tissue of a defined shape with fewer punctures in its immediate surround than current practice
5. Reducing Radiation exposure to healthcare workers, as most electro-anaesthesia is performed under fluoroscopy limiting exposure is advantageous.
6. In limiting the activation time the patient discomfort is limited commensurately.
7. increasing safety by virtue of faster placement needing less accuracy providing bigger lesions to account for individual enervation with fewer needles and consequently better infection control.
8. increasing useability and thus allows lesser skilled clinicians to perform spinal electro-anaesthesia. This both improves patient access to such therapy and increases competition which over time again suppresses costs to patients and healthcare institutions.
9. reducing the learning time required by clinicians to perform the procedure with safety reducing costs of teaching and increasing safety for patients.
10. allowing new procedures to be executed such as therapy for the sacroiliac joint for which there is presently no therapy and where analgesia is of little effect.
11. providing an RF generator and associated electrodes and probe equipment small enough and sterilisable allowing location entirely within the sterile boundary. The clinician thus has complete control of surgical procedures with the flexibility to attach or detach probe connectivity according to anatomical presentation. Orthopaedic surgery and prosthetic placement with ERP stimulation to guide denervation is one such instance. While chemical or gaseous sterilisation of this embodiment is implied presently, no theoretical limits should prohibit 120 deg C. autoclaving of future embodiments.

12. providing such device functionality as herein described may allow electro-anaesthesia procedures to be developed for much if not all muscular-skeletal pain.

13. improving reproducibility and consequent expansion of therapies by providing procedure configuration files which provide the clinicians with setup and placements for recognised and repetitive procedures, particularly with the manifold or formwork described herein. With the repetitive manual placements presently practiced such automation is impractical.

The term "comprising" (and its grammatical variations) as used herein is used in the inclusive sense of "including" or "having" and not in the exclusive sense of "consisting only of".

The invention claimed is:

1. A device for supplying RF electrical power to biological tissue, comprising
    (a) an RF generator device with a parallel-resonant output stage comprising a tank circuit inductively coupled to said RF generator device,
    (b) a plurality of electrodes connected to said resonant output stage, the electrodes being capable of being placed in biological tissue, and
    (c) a selector mechanism operating a plurality of switches capable of connecting said electrodes across the outputs of said tank circuit in any possible combination without disconnecting said electrodes from the outputs of said tank circuit operating under continuous RF excitation,
    wherein substantially all of the resistance in said resonant output stage consists of said biological tissue,
    wherein a DC voltage is the sole determinant of the maximum RF power, and
    wherein there is no processor control function to adjust either the current or voltage of said RF power.

2. The device of claim 1, wherein said resonant output stage oscillates with a phase lag relative to said RF generator device.

3. The device of claim 1, wherein the output power level of said RF generating device is self-regulating and relatively insensitive to changes in the impedance of the biological tissue between the electrodes such that percentage changes in output power level are less than percentage changes in impedance.

4. The device of claim 1, wherein the output power level of said RF generating device is self-regulating and insensitive to changes that occur during dynamic switching of said selector mechanism, such that said output power is limited during transient switching without disconnecting said electrodes from the outputs of said tank circuit operating under continuous RF excitation.

5. The device of claim 1, wherein the orientation and degree of insertion of at least four of said electrodes define a volume including the region between any pair of the four electrodes, and said volume is bounded by further impedance measurement electrodes used to monitor adjacent tissues and ensure that they are excluded from hyperthermic effects.

6. The device of claim 1, further comprising a sensor configured to measure the RF current between a selected pair of said electrodes while voltage is supplied from said RF generator device, wherein the RF current is measured at the frequency of the RF generator device.

7. The device of claim 6, wherein said selected pair of electrodes is activated only momentarily for the purpose of measuring current distribution and impedance such that no coagulum forms between the selected pair of electrodes during the momentary activation.

8. The device of claim 1, further comprising a plurality of temperature sensing means for measuring temperature in said biological tissue.

9. The device of claim 1, wherein the RF electrical power supplied to said biological tissue is sufficient to desiccate said biological tissue to the point of denervation but not to damage the inherent fiber structure.

10. The device of claim 1, wherein the RF electrical power supplied to said biological tissue is proportional to a DC control voltage.

11. A method for inducing desiccation of elongate nerve tissue in mammalian tissue by producing a thermal lesion, comprising
    (a) inserting a plurality of electrodes into mammalian tissue containing elongate nerve tissue,
    (b) selecting the orientation and degree of insertion of at least four of said electrodes to define a volume including at least a substantial portion of said elongate nerve tissue, and
    (c) applying a controlled distribution of RF current between pairs or sets of said electrodes for a discharge period to heat said volume to the extent of effective desiccation,
    wherein said electrodes are connected to an RF generator device with a parallel-resonant output stage comprising a tank circuit inductively coupled to said RF generator device, and a selector mechanism operating a plurality of switches capable of connecting said electrodes across the outputs of said tank circuit in any possible combination without disconnecting said electrodes from the outputs of said tank circuit operating under continuous RF excitation, and
    wherein substantially all of the resistance in said resonant output stage consists of said biological tissue.

12. The method of claim 11, wherein said elongate nerve tissue is sufficiently desiccated to produce an anesthetic effect.

13. The method of claim 11, further comprising measuring the distribution of changing impedances in said mammalian tissue by sensing alternating current during momentary activation of selected electrodes such that no coagulum forms between the selected pair of electrodes during the momentary activation.

14. The method of claim 13, wherein the electrodes activated momentarily are not the same as those used for heating.

15. The method of claim 13, wherein selected electrodes are activated alternately with (1) power and duration sufficient for heating said volume, and (2) momentary activation sufficient for current sensing but not for heating.

16. The method of claim 13, wherein said measuring the distribution of changing impedances is used to represent the accumulation of coagulum around individual electrodes, and wherein a uniform distribution of coagulum between active discharge electrodes is created by adapting the activation of electrode patterns.

17. The method of claim 13, further comprising the steps of
    (d) testing the perfusion of said thermal lesion by a method comprising the steps of
        (i) waiting for a period of time longer than the RF discharge period to allow re-perfusion of electrolytes into said volume, and
        (ii) measuring changes in tissue impedance; and
    (e) re-energizing said electrodes if significant measured changes in tissue impedance occur.

18. The method of claim 11, wherein the frequency of said RF current is between about 100 kHz and 700 kHz.

19. The method of claim 18, wherein said frequency is approximately 500 kHz.

20. The method of claim 11, further comprising repeating steps (a)-(c) at intervals of from about 6 months to about 2 years.

21. The method of claim 11, wherein the volume including at least a substantial portion of said elongate nerve tissue is bounded by electrodes excluding other tissue from hyperthermic effects.

22. The method of claim 11, wherein said electrodes are mounted in probes with hollow cannulas through which chemicals such as anesthetics or other therapeutic or ablative fluids can be injected.

* * * * *